(12) United States Patent
Peng et al.

(10) Patent No.: US 12,201,345 B2
(45) Date of Patent: Jan. 21, 2025

(54) ELECTRODE FOR ELECTROSURGICAL INSTRUMENTS

(71) Applicants: YISI (SUZHOU) MEDICAL TECHNOLOGY CO., LTD., Jiangsu (CN); SHANGHAI YISI MEDICAL TECHNOLOGY CO., LTD., Shanghai (CN)

(72) Inventors: Xinyu Peng, Shanghai (CN); Yu Zhang, Shanghai (CN); Xiufeng Shi, Shanghai (CN); Honglin Nie, Shanghai (CN)

(73) Assignees: YISI (SUZHOU) MEDICAL TECHNOLOGY CO., LTD., Jiangsu (CN); SHANGHAI YISI MEDICAL TECHNOLOGY CO., LTD., Shanghai (CN)

(*) Notice: Subject to any disclaimer, the term of this patent is extended or adjusted under 35 U.S.C. 154(b) by 1028 days.

(21) Appl. No.: 16/480,603

(22) PCT Filed: Jan. 3, 2018

(86) PCT No.: PCT/CN2018/070087
§ 371 (c)(1),
(2) Date: Jul. 24, 2019

(87) PCT Pub. No.: WO2018/137477
PCT Pub. Date: Aug. 2, 2018

(65) Prior Publication Data
US 2019/0388140 A1 Dec. 26, 2019

(30) Foreign Application Priority Data

Jan. 24, 2017 (CN) .......................... 201710060077.1

(51) Int. Cl.
*A61B 18/00* (2006.01)
*A61B 18/12* (2006.01)
(Continued)

(52) U.S. Cl.
CPC ............ *A61B 18/14* (2013.01); *A61L 31/126* (2013.01); *A61L 31/14* (2013.01); *H01B 1/22* (2013.01);
(Continued)

(58) Field of Classification Search
CPC .......... A61B 18/14; A61B 2018/00077; A61B 2018/0013; A61B 2018/00136;
(Continued)

(56) References Cited

U.S. PATENT DOCUMENTS 5,197,962 A * 3/1993 Sansom ................. A61B 18/14
606/49
5,713,895 A * 2/1998 Lontine .............. A61B 18/1402
606/49

(Continued)

OTHER PUBLICATIONS

Terrones, M., etc.. (2010). Graphene and graphite nanoribbons: Morphology, properties, synthesis, defects and applications. Nano Today, 5(4), 351-372. (Year: 2010).*

(Continued)

*Primary Examiner* — Joseph A Stoklosa
*Assistant Examiner* — Annie L Shoulders
(74) *Attorney, Agent, or Firm* — Venable LLP

(57) ABSTRACT

The present application relates to a monopolar electrode and a bipolar electrode that are used for electrosurgical instruments. The monopolar electrode and the bipolar electrode each include a conductive non-stick coating which is made by doping graphene and/or metal particles in a PTFE (polytetrafluoroethylene) base material. The present application also relates to a preparation method of a composite material (Continued)

forming the conductive non-stick coating. Since PTFE itself can prevent adhesion, the conductivity of PTFE can be improved by doping various conductive materials. After the composite material coating formed thereby covers a metal electrode, it is ensured that the working region and work energy of an electrotome are not reduced, the electrical conductivity of the electrode can be guaranteed, not only the blood coagulation effect of the electrotome is not affected but also the adhesion of the electrode on a tissue can be reduced. Furthermore, the structure is simple, and manufacturing is easy.

17 Claims, 1 Drawing Sheet

(51) Int. Cl.
  *A61B 18/14* (2006.01)
  *A61L 31/12* (2006.01)
  *A61L 31/14* (2006.01)
  *H01B 1/22* (2006.01)
  *H01B 1/24* (2006.01)

(52) U.S. Cl.
  CPC ...... *H01B 1/24* (2013.01); *A61B 2018/00077* (2013.01); *A61B 2018/0013* (2013.01); *A61B 2018/00136* (2013.01); *A61B 2018/00607* (2013.01); *A61B 2018/1253* (2013.01); *A61B 2018/126* (2013.01); *A61L 2420/02* (2013.01)

(58) Field of Classification Search
  CPC ...... A61B 2018/1253; A61B 2018/126; A61L 31/126; A61L 31/14; A61L 2420/02; H01B 1/22; H01B 1/24
  See application file for complete search history.

(56) References Cited

U.S. PATENT DOCUMENTS

| | | | |
|---|---|---|---|
| 2002/0111622 A1* | 8/2002 | Khandkar | A61B 18/14 606/45 |
| 2013/0110108 A1* | 5/2013 | Davison | A61B 18/1402 606/49 |
| 2013/0226177 A1* | 8/2013 | Brandt | A61B 18/1442 606/49 |
| 2014/0030590 A1* | 1/2014 | Wang | H01M 4/366 977/734 |
| 2014/0052120 A1* | 2/2014 | Benscoter | A61L 29/02 606/41 |
| 2015/0297292 A1* | 10/2015 | Sutermeister | A61M 37/00 606/41 |
| 2015/0309453 A1* | 10/2015 | Yang | G03G 15/2057 252/502 |
| 2016/0035456 A1* | 2/2016 | Sauro | H01B 1/24 252/511 |
| 2016/0213395 A1* | 7/2016 | Anim | A61L 31/041 |
| 2017/0119425 A1* | 5/2017 | Hibner | A61B 90/03 |
| 2017/0154975 A1* | 6/2017 | Liu | H01L 21/0212 |
| 2018/0036060 A1* | 2/2018 | Wegrzyn, III | A61B 18/082 |
| 2019/0262068 A1* | 8/2019 | Tang | A61B 18/1492 |
| 2020/0038098 A1* | 2/2020 | Sartor | A61B 18/1445 |
| 2020/0188660 A1* | 6/2020 | Franke | A61B 5/1107 |

OTHER PUBLICATIONS

Nair, S. S., Saha, T., Dey, P., & Bhadra, S. (2020). Thermal oxidation of graphite as the first step for graphene preparation: Effect of heating temperature and time. Journal of Materials Science, 56(5), 3675-3691. (Year: 2020).*
Suh, J., & Bae, D. (2016). Mechanical properties of polytetrafluoroethylene composites reinforced with graphene nanoplatelets by solid-state processing. Composites Part B: Engineering, 95, 317-323. https://doi.org/10.1016/j.compositesb.2016.03.082 (Year: 2016).*
Güler, Ö., & Bağc, N. (2020). A short review on mechanical properties of graphene reinforced metal matrix composites. Journal of Materials Research and Technology, 9(3), 6808-6833. https://doi.org/10.1016/j.jmrt.2020.01.077 (Year: 2020).*
Prashantha Kumar, H. G., & Anthony Xavior, M. (2017). Processing and characterization of al 6061—graphene nanocomposites. Materials Today: Proceedings, 4(2), 3308-3314. https://doi.org/10.1016/j.matpr.2017.02.217 (Year: 2017).*
Processing and Characterization of Al 6061—Graphene Nanocomposites (Year: 2017).*
Mechanical properties of polytetrafluoroethylene composites reinforced with graphene nanoplatelets by solid-state processing (Year: 2016).*
Sattar, "Current Review on Synthesis, Composites and Multifunctional Properties of Graphene", Topics in Current Chemistry (2019) 377:10, Mar. 14, 2019, pp. 1-45.
Hauert et al., "An overview on diamond-like carbon coatings in medical applications", Surface & Coatings Technology 233 (2013), Apr. 12, 2013, pp. 119-130.
Robertson, "Properties of diamond-like carbon", Surface and Coatings Technology, 50 (1992), Aug. 25, 1991, pp. 185-203.
Papageorgiou et al., "Mechanical properties of graphene and graphene-based nanocomposites", Progress in Materials Science 90 (2017), Jul. 21, 2017, pp. 75-127, School of Materials and National Graphene Institute, The University of Manchester, Manchester, UK.
Luo et al., "Diamond and diamond-like carbon Mems", Journal of Micromechanics and Microengineering, Jun. 28, 2007, Pages S147-S163, Iop Publishing, United Kingdom.
Bewilogua et al., "History of diamond-like carbon films—From first experiments to worldwide applications", Surface & Coatings Technology 242 (2014), Jan. 25, 2014, pp. 214-225, Germany.
Zeng et al., "Diamond-like carbon (DLC) films as electrochemical electrodes", Diamond & Related Materials 43 (2014), Jan. 9, 2014, pp. 12-22.
Lee et al., "Comparison of frictional forces on graphene and graphite", Nanotechnology, Jul. 21, 2009, pp. 1-6, vol. 20, IOP Publishing, UK.
Neto et al., "The electronic properties of graphene", Reviews of Modern Physics, Jan. 14, 2009, pp. 109-162, vol. 81, American Physical Society.
Alofi et al., "Thermal conductivity of graphene and graphite", Physical Review B 87, 115421, Mar. 18, 2013, pp. 1-10, American Physical Society.

* cited by examiner

ELECTRODE FOR ELECTROSURGICAL INSTRUMENTS

CROSS-REFERENCE TO RELATED APPLICATIONS

This application is a national stage entry of International Patent Application No. PCT/CN2018/070087, filed Jan. 3, 2018 (published in Chinese on Aug. 2, 2018, as WO 2018/137477 A1), which claims priority to Chinese Patent Application No. 201710060077.1, filed Jan. 24, 2017, each of which is hereby expressly incorporated by reference in its entirety.

TECHNICAL FIELD

The present application relates to the field of medical instruments, and particularly relates to an electrode used for electrosurgical instruments.

BACKGROUND

A high-frequency electrotome (electrosurgical system) is an electrosurgical instrument for cutting a tissue through replacement of a mechanical scalpel. Since 1920s, there have been commercialized high-frequency electrotome products for surgical operation (see Progress of Electrosurgical Instrument, Hao You, Qian Yang, Chinese Journal of Medical Instruments, No. 4, 2012). It can separate and coagulate tissues of an organism by heating the tissues when high-frequency high-voltage current produced by the tip of the effective electrode contacts with the organism, thus achieving the purposes of cutting and hemostasis. Compared with the mechanical scalpel, the high-frequency electrotome is faster in cutting speed and better in hemostasis effect, and can be not only directly used in surgery but also cooperatively used in laparoscopy and other endoscopic surgeries.

However, when in work, the high-frequency electrotome generates high temperature, which typically leads to large tissue heat injury and often causes eschar in clinic. If the eschar is adhered to the instrument, it will not only affect the continuous use of the instrument, but also sometimes lead to the destruction of the hemostatic tissue to cause more bleeding when the instrument is pulled.

In order to avoid tissue adhesion, there have been some related designs at present. Some of the designs are that an impedance is dynamically detected through a main engine, and when the impedance reaches a threshold, energy output actively stops or decreases, or a user is remained to stop energy output, and then reduce tissue adhesion caused by redundant heat injury. Although such the design can reduce tissue adhesion, there is a need for the main engine to have high-grade feedback regulation functions, and cost is very high.

In the prior art, some designs are that some anti-sticking texture shapes are designed on an electrode of a scalpel head of an instrument contacting with tissues (see: Bionic Desorption Study of High Frequency Electrotome Surface of Minimally Invasive Surgical Instruments, Huina Cao, Jilin University, 2015), or partial coatings are made (see U.S. Pat. No. 5,713,895, named Partially Coated Electrodes"), or the electrode is either hollowed out or embedded in a nonmetallic material such as ceramics (see U.S. Pat. No. 7,458,972 B2 from Covidien AG, named "Electrosurgical Electrode Having A Non-Conductive Porous Ceramic Coating"). However, the overall design direction of these solutions is to reduce the contact time or contact area between electrodes and tissues. But, in the application of large vessels closure, it is necessary to guarantee sufficient contact area and time between the electrodes and the large vessels to ensure the complete closure of large vessels. Therefore, it may not always be beneficial in some applications to prevent adhesion simply by controlling the contact time or contact area between the electrodes and the tissues.

In ultrasound energy surgery, there has been a practice that a PTFE coating is added to the scalpel head to prevent tissue adhesion (see Patent CN103260533A from ETHICON ENDO-SURGERY Company, named "surgical instruments"). Because the cutter head of an ultrasonic scalpel instrument is not conductive, addition of the non-conductive PTFE coating does not affect the normal work of the ultrasonic scalpel instrument. However, a part of the cutter head of the electrotome instrument is an electrode, and the electrotome instrument itself works via electric conductivity, thus simple addition of the PTFE coating cannot drive working.

SUMMARY

In order to solve the above technical problem, the present application provides an electrode used for electrosurgical instruments. In the disclosure, a conductive non-stick coating is added on the electrode of the existing high-frequency electrotome instrument. When the electrosurgical instrument is applied to perform surgery, adhesion of tissues is reduced under the condition of ensuring complete cutting or closing tissues, so that the surgical operation is more fluent.

According to one aspect of the present application, provided is a monopolar electrode used for electrosurgical instruments, comprising: a metal electrode, a first conductive coating located on the surface of the metal electrode and a conductive metal part, wherein, the first conductive coating is used for contacting with human tissues, the metal part is electrically connected with the electrosurgical instrument, and the first conductive coating is a non-stick coating.

The present application can directly adopt the monopolar electrode used for electrosurgical instruments in the prior art, wherein, the non-stick conductive coating is added on the metal electrode so that the electrode not only can be conductive to complete the function of the electrosurgical instrument when contacting with a human tissue, but also can avoid tissue adhesion in surgery.

Further, the monopolar electrode also comprises a sunken groove located between the first conductive coating and the metal part, and the sunken groove is used for locking and latching the monopolar electrode.

Further, the first conductive coating entirely covers the metal electrode or partially covers the metal electrode.

Further, the first conductive coating is made by doping various conductive materials in a PTFE base material. For example, graphene and/or metal particles are doped in the PTFE base material. PTFE itself can prevent adhesion, but is not conductive, and therefore the conductivity of PTFE can be improved by doping various conductive materials. After a composite material coating formed thereby covers the metal electrode, the conductivity of the electrode can be ensured, and the adhesion of the electrode on tissues can be reduced.

In one embodiment, the first conductive coating is made of a composite material formed by doping graphene in PTFE (polytetrafluoroethylene). Such the composite material can has relatively high conductivity, and meanwhile has the characteristics of PTFE, such as abrasion resistance and no adhesion.

In one embodiment, the material of the metal electrode is the same as that of the metal part.

In one particular embodiment, the whole monopolar electrode is loaded in the holding portion of the monopolar instrument of the electrosurgical system, or serves as one part of the monopolar instrument. The monopolar instrument is connected with the high-frequency generator of the electrosurgical system through wire cables; the high-frequency generator generates high frequency current which is conducted to the first conductive coating via the conductive metal part; because the first conductive coating is conductive, the high frequency current is conducted to a human tissue contacting with the first conductive coating; after flowing through a human body, the current returns back to the high-frequency generator through a negative plate contacting with the human body.

According to another aspect of the present application, provided is a bipolar electrode used for electrosurgical instruments, comprising: a negative electrode, a positive electrode, a second conductive coating located on the surface of the positive electrode, and a connection component, wherein, the negative electrode and the positive electrode are used for contacting with human tissues, and the connection component can be electrically connected with the electrosurgical instrument; the second conductive coating is a non-stick coating.

Like the above monopolar, the present application can directly adopt the bipolar metal electrode of the electrosurgical instrument in the prior art. The non-stick conductive coating is added on the metal positive electrode, so that the electrode not only can be conductive to complete the function of the electrosurgical instrument when contacting with the human tissues, but also can avoid tissue adhesion in surgery.

Further, the second conductive coating entirely covers the positive electrode or partially covers the positive electrode.

Further, the second conductive coating is made by doping various conductive materials in a PTFE base material. For example, graphene and/or metal particles are doped in the PTFE base material. PTFE itself can prevent adhesion, but is not conductive, and therefore the conductivity of PTFE can be improved by doping various conductive materials. After a composite material coating formed thereby covers the metal electrode, the electrical conductivity of the electrode can be ensured, and the adhesion of the electrode on tissues can be reduced.

In one embodiment, the second conductive coating is made of a composite material formed by doping graphene in PTFE (polytetrafluoroethylene).

In one particular embodiment, the connection component is a sleeve; at least 2 wires are contained in the sleeve; the negative electrode and the positive electrode are each conducted with one wire. The bipolar electrode is connected with the high-frequency generator of the electrosurgical system through wires, and the high-frequency generator generates high frequency current which is transferred to the bipolar electrode via the wires.

In one particular embodiment, the second conductive coating completely covers the positive electrode 5. In this case, the high-frequency generator emits high frequency current which flows into the positive electrode via one wire, and then is transferred to human tissues through the second conductive coating; after flowing through the human body, the current returns back again to the high-frequency generator through the negative electrode and the wire connected therewith.

In another particular embodiment, the second conductive coating partially covers the positive electrode. In this case, the part of the positive electrode on which the second conductive coating covers contacts with the human tissue; the part of the positive electrode on which the second conductive coating does not cover directly contacts with the human tissue; the high-frequency generator emits high frequency current which flows into the positive electrode via one wire; one part of the high frequency current is transferred to the human tissue through the second conductive coating, and the other part of the high frequency current is directly transferred to the human tissue; after flowing through a human body, the current returns back to the high-frequency generator through the negative electrode and the wire connected therewith.

The composite material forming the above first conductive coating and second conductive coating can be prepared by using multiple methods. In one particular embodiment, firstly, PTFE aqueous dispersions and oxidized graphene are doped in aqueous solution through electrostatic adsorption, and then a hybrid material is coated after the oxidized graphene is reduced.

Preferably, when in doping, the content of PTFE particles in the PTFE aqueous dispersions is 20 wt %, and the content of the oxidized graphene in the PTFE aqueous dispersions is 2 wt %.

The thicknesses of the first conductive coating 1 and the second conductive coating 6 can be set according to the need. In one particular embodiment, the thickness of the coating is less than 0.05 mm, preferably, the thickness of the coating is controlled to be between 0.003 mm and 0.020 mm.

In the present application, the conductive non-stick coating is provided on the existing monopolar electrode or bipolar electrode, and the conductive non-a stick coating is made by doping graphene and/or metal particles in the PTFE base material. Since PTFE itself can prevent adhesion, the conductivity of PTFE can be improved by doping various conductive materials. After the composite material coating formed thereby covers the metal electrode, it is ensured that the electrotome working region and work energy are not reduced, the electrical conductivity of the electrode is guaranteed, the blood coagulation effect of the electrotome is not affected, and the adhesion of the electrode on the tissue can also be reduced. Furthermore, the structure is simple, and manufacture is easy.

The technical solution of the present application mainly solves the problem that in the process of using the electrosurgical instrument, the current acts on the human tissues so that tissue protein is solidified and adhered to the instrument electrode, and then the normal use of the instrument is affected. Compared with the existing technology that the tissue adhesion is controlled by the main engine, this innovation does not require the main engine to have high-grade feedback regulation functions, and the main engine of the ordinary high-frequency electrotome can also be used, thereby greatly reducing the cost. In addition, compared with the existing technology of the structure design of the instrument electrode, the present application ensures that the work region and work energy of the electrotome are not reduced, and the blood coagulation effect of the electrotome is not affected.

REFERENCE NUMBERS OF PARTS IN FIGURES ARE AS FOLLOWS:

1, coating part; 2, sunken groove; 3, metal part; 4, negative electrode; 5, positive electrode; 6, coating part of positive electrode; 7, sleeve

DESCRIPTION OF THE EMBODIMENTS

Next, the technical solutions in embodiments of the disclosure will be clearly and completely described. Apparently, the described embodiments are only one part of embodiments in the present application, but not all the embodiments. Based on embodiments of the present application, other embodiments made by those of ordinary skill in the art without any creative efforts all belong to the scope of protection of the present application.

Figure 1:
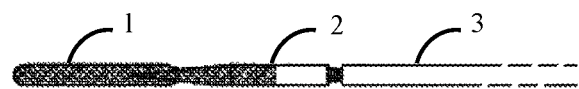
FIG. 1 is a stereo view of a monopolar electrode containing a coating according to an embodiment of the disclosure.

Referring to FIG. 1, a stereo view of a monopolar electrode containing a coating according to an embodiment of the disclosure is shown. The monopolar electrode is used for electrode surgical instruments, preferably for a high-frequency electrode knife. The monopolar electrode, as the head of the high-frequency electrode knife, applies cutting or electrocoagulation energy to tissues of a patient. The high-frequency electrode knife is generally provided with a high-frequency generator, a circuit board and a power source interface, wherein, the high-frequency generator provides high-frequency current, the circuit board drives and controls the head of the electrode knife to provide adaptive electric power for the head of the electrode knife, thereby transmitting the proper electrically cut or coagulated energy to the head of the electrode knife.

The monopolar electrode in FIG. 1 includes a metal electrode, a first conductive coating 1 located on the surface of the metal electrode, a conductive metal part 3 and a sunken groove 2 located between the first conductive coating 1 and the metal part 3, wherein, the first conductive coating 1 is used for contacting human tissues, the metal part 3 is electrically connected with the electrosurgical instrument, preferably, the metal part 3 is loaded to the head of the electrosurgical instrument and sufficiently contacts with a conductor in the instrument, the sunken groove 2 is used for locking and latching the monopolar electrode. The first conductive coating 1 is a non-stick coating.

In one embodiment, the material of the metal electrode is the same as that of the metal part 3.

In practical application, the whole monopolar electrode can be loaded to the holding portion of the monopolar instrument of the electrosurgical system, or serves as one component of the monopolar instrument. The monopolar instrument is connected with the high-frequency generator of the electrosurgical system through wire cables; the high-frequency generator generates high frequency current which is conducted to the first conductive coating 1 via the conductive metal part 3; because the first conductive coating 1 is conductive, the high frequency current is conducted to the first conductive coating 1 to contact with the human tissues; after flowing through the human body, the current returns back to the high-frequency generator through a negative electrode.

Figure 2:
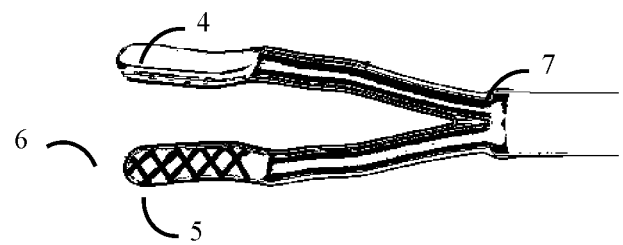
FIG. 2 is a stereo view of a bipolar electrode containing a coating according to another embodiment of the disclosure.

Referring to FIG. 2, a stereo view of a bipolar electrode containing a coating according to another embodiment of the disclosure is shown. The bipolar electrode is used for electrosurgical instruments, preferably for a high-frequency electrotome. The bipolar electrode, as the head of the high-frequency electrode knife, applies cutting or electrocoagulation energy to human tissues. The high-frequency electrode knife is generally provided with a high-frequency generator, a circuit board and a power source interface, wherein, the high-frequency generator provides high-frequency current, the circuit board drives and controls the head of the electrode knife to provide adaptive electric power for the head of the electrode knife, thereby transmitting the proper electrically cut or coagulated energy to the head of the electrode knife.

The bipolar electrode in FIG. 2 includes a negative electrode 4, a positive electrode 5, a second conductive coating 6 on the surface of the positive electrode 5 and a sleeve 7, wherein, the negative electrode 4 and the positive electrode 5 are used for contacting with human tissues, the sleeve 7 is electrically connected with the electrosurgical instrument, preferably, the sleeve 7 is loaded to the head of the electrosurgical instrument and sufficiently contacts with a conductor in the instrument. The second conductive coating 6 is a non-stick coating. In this embodiment, the second conductive coating 6 is only provided on the surface of the positive electrode 5, and in other embodiments, the second conductive coating 6 can be provided on the surface of the negative electrode 4, or the surfaces of the positive electrode 5 and the negative electrode 4 are both provided with the second conductive coatings 6.

The second conductive coating 6 can entirely cover the positive electrode 5, or can also partially cover the positive electrode 5.

In one particular embodiment, at least two wires are contained in the sleeve 7, the negative electrode 4 and the positive electrode 5 are each conducted with one wire.

In one particular embodiment, the second conductive coating 6 completely covers the positive electrode 5. In this case, the high-frequency generator emits high frequency current which flows into the positive electrode 5 via one wire, and then is transferred to the human tissues through the second conductive coating 6; after flowing through the human body, the current returns back to the high-frequency generator through the negative electrode 4 and the wire connected therewith.

In another particular embodiment, the second conductive coating 6 partially covers the positive electrode 5. In this case, the part of the positive electrode 5 on which the second conductive coating 6 covers contacts with the human tissue through the second conductive coating 6; the part of the positive electrode 5 on which the second conductive coating 6 does not cover directly contacts with the human tissue; the high-frequency generator emits high frequency current which flows into the positive electrode 5 via one wire; one part of the high frequency current is transferred to the human tissues through the second conductive coating 6, and the other part of the high frequency current is directly transferred to the human tissues; after flowing through the human body, the current returns back to the high-frequency generator through the negative electrode 4 and the wire connected therewith.

The first conductive coating 1 and the second conductive coating 6 preferably adopt PTFE doped graphene. Such the composite material can have relatively high conductivity, and meanwhile has the characteristics of abrasion resistance, no adhesion and the like.

The composite material forming the first conductive coating 1 and the second conductive coating 6 can be prepared by using multiple methods. In one particular embodiment, firstly, PTFE aqueous dispersions and oxidized graphene are doped in aqueous solution through electrostatic adsorption, and then a hybrid material is coated after the oxidized graphene is reduced.

Preferably, when in doping, the content of PTFE particles in the PTFE aqueous dispersions is 20 wt %, and the content of the oxidized graphene in the PTFE aqueous dispersions is 2 wt %.

The thicknesses of the first conductive coating 1 and the second conductive coating 6 can be set according to a need. In one particular embodiment, the thickness of the coating is less than 0.05 mm, preferably, the thickness of the coating is controlled to be between 0.003 mm and 0.020 mm.

The present application mainly solves the problems that in the process of using the electrosurgical instrument, the current acts on the human tissues so that tissue protein is solidified and adhered to the instrument electrode, and then the normal use of the instrument is affected. Compared with the existing technology that the tissue adhesion is controlled by the main engine, this innovation does not require the main engine to have high-grade feedback regulation functions, and the main engine of the ordinary high-frequency electrotome can also used, thereby greatly reducing the cost. In addition, compared with the existing technology of the structure design of the instrument electrode, the present application ensures that the electrotome work region and work energy are not reduced, and the blood coagulation effect of the electrotome is not affected.

The above descriptions are only several embodiments of the present application, of course, cannot thereby limit the claim scope of the present application, and therefore equivalent changes made according to the claims of the present application are still included in the scope of the present application.

What is claimed is:

1. A monopolar electrode used for an electrosurgical instrument, comprising: a metal electrode, a first conductive coating located on the surface of the metal electrode and a conductive metal part,
    wherein, the first conductive coating is used for contacting with human tissues, and the metal part is electrically connected with the electrosurgical instrument; wherein, the first conductive coating is a non-stick coating; and wherein, the first conductive coating is made by doping graphene which has high conductivity relative to metal particles in a PTFE base material, and
    wherein the first conductive coating covering a first portion of the metal electrode is configured to be in direct physical and electrical contact with the human tissues, and a second portion of the metal electrode not covered by the first conductive coating is configured to be in direct physical and electrical contact with the human tissues.

2. The monopolar electrode according to claim 1, also comprising a sunken groove located between the first conductive coating and the metal part, wherein, the sunken groove is used for locking and latching the monopolar electrode.

3. The monopolar electrode according to claim 1, wherein, the monopolar electrode is loaded in a holding portion of a monopolar instrument of the electrosurgical instrument, or the monopolar electrode serves as one part of the monopolar instrument.

4. The monopolar electrode according to claim 3, wherein, the monopolar instrument is connected with a high-frequency generator of the electrosurgical instrument through wire cables; the high-frequency generator generates high frequency current which is conducted to the first conductive coating via the conductive metal part and then to the human tissues contacting with the first conductive coating; after flowing through the human tissues, the current returns back to the high-frequency generator through a negative plate contacting with the human tissues.

5. The monopolar electrode according to claim 1, wherein, the first conductive coating is made by doping metal particles in the PTFE base material.

6. The monopolar electrode according to claim 1, wherein, the thickness of the coating is less than 0.05 mm.

7. The monopolar electrode according to claim 6, wherein, the thickness of the coating is controlled to be between 0.003 mm and 0.020 mm.

8. A bipolar electrode used for an electrosurgical instrument, comprising: a negative electrode, a positive electrode, a second conductive coating located on the surface of the positive electrode and/or the negative electrode, and a connection component, wherein, the negative electrode and the positive electrode are used for contacting with human tissues, and the connection component is electrically connected with the electrosurgical instrument; wherein, the second conductive coating is a non-stick coating, wherein, the second conductive coating is made by doping graphene which has high conductivity relative to metal particles in a PTFE base material, and
    wherein the second conductive coating covering a first portion of the positive electrode is configured to be in direct physical and electrical contact with the human tissues, and a second portion of the positive electrode not covered by the second conductive coating is configured to be in direct physical and electrical contact with the human tissues.

9. The bipolar electrode according to claim 8, wherein, the connection component is a sleeve; at least 2 wires are contained in the sleeve; the negative electrode and the positive electrode are each conducted with one wire; the bipolar electrode is connected with a high-frequency generator of the electrosurgical instrument through wires; the high-frequency generator generates high frequency current which is transferred to the bipolar electrode via wires.

10. The bipolar electrode according to claim 8, wherein, a high-frequency generator emits high frequency current which flows into the positive electrode via one wire and then is transferred to human tissues through the second conductive coating; after flowing through the human tissues, the current returns back to the high-frequency generator through the negative electrode and the wire connected therewith.

11. The bipolar electrode according to claim 8, wherein, a high-frequency generator emits high frequency current which flows into the positive electrode via one wire, one part of the high frequency current is transferred to the human tissues through the second conductive coating, and the other part of the high frequency current is directly transferred to the human tissues; after flowing through the human tissues, the current returns back again to the high-frequency generator through the negative electrode and the wire connected therewith.

12. The bipolar electrode according to claim 8, wherein, the second conductive coating is made by doping metal particles in the PTFE base material.

13. The bipolar electrode according to claim 8, wherein, the thickness of the coating is less than 0.05 mm.

14. The bipolar electrode according to claim 13, wherein, the thickness of the coating is controlled to be between 0.003 mm and 0.020 mm.

15. A preparation method of a composite material, the composite material being used for forming the first conductive coating according to claim 1, and the preparation method comprising the following steps:
  (1) doping PTFE aqueous dispersions and oxidized graphene in aqueous solution through electrostatic adsorption;
  (2) coating a hybrid material after reducing the oxidized graphene.

16. The preparation method of claim 15, wherein, in the step (1), when in doping, content of PTFE particles in the PTFE aqueous dispersions is 20 wt % and content of the oxidized graphene in the PTFE aqueous dispersions is 2 wt %.

17. A preparation method of a composite material, the composite material being used for forming the second conductive coating according to claim 8, and the preparation method comprising the following steps:
  (3) doping PTFE aqueous dispersions and oxidized graphene in aqueous solution through electrostatic adsorption;
  (4) coating a hybrid material after reducing the oxidized graphene.

\* \* \* \* \*